United States Patent [19]

McMullen

[11] Patent Number: 4,788,144
[45] Date of Patent: Nov. 29, 1988

[54] FERMENTATION PROCESS FOR THE HIGH LEVEL PRODUCTION OF SWINE GROWTH

[75] Inventor: James R. McMullen, Terre Haute, Ind.

[73] Assignee: International Minerals & Chemical Corp., Terre Haute, Ind.

[21] Appl. No.: 751,976

[22] Filed: Jun. 28, 1985

[51] Int. Cl.$^4$ .................. C12P 21/02; C12N 15/00; C12N 1/00
[52] U.S. Cl. .................. 435/70; 435/172.3; 435/320; 435/813; 435/818; 935/43
[58] Field of Search .............. 435/68, 70, 172.3, 813, 435/818; 935/43

[56] References Cited

U.S. PATENT DOCUMENTS

| | | | |
|---|---|---|---|
| 4,167,450 | 9/1979 | Chesbro et al. | 435/813 |
| 4,317,882 | 3/1982 | Hoviguchi et al. | 435/818 |
| 4,511,502 | 4/1985 | Builder et al. | 260/112 |
| 4,512,922 | 4/1985 | Jones et al. | 260/112 |
| 4,518,526 | 5/1985 | Olson | 260/112 |
| 4,569,790 | 2/1986 | Koths | 435/68 |

FOREIGN PATENT DOCUMENTS

| | | |
|---|---|---|
| 0076037 | 4/1983 | European Pat. Off. . |
| 0103395 | 3/1984 | European Pat. Off. . |
| 0104920 | 4/1984 | European Pat. Off. . |
| 131843 | 1/1985 | European Pat. Off. . |

OTHER PUBLICATIONS

Queen, J. of Molecules and Applied Genetics, vol. 1, pp. 1–10, 1983.
Bauer et al., Biotechnology and Bioengineering, vol. XVI, pp. 933–941 (1974).
Hopkins, Chemical Abstracts, vol. 95:148688n, 1981.
Seeburg et al., DNA, vol. 2, No. 1, pp. 37–45 (1983).

Primary Examiner—Alvin E. Taneholtz
Attorney, Agent, or Firm—Bernard, Rothwell & Brown

[57] ABSTRACT

A high-density fermentation process for high yield production of swine growth hormone by transformant *E. coli* is described. The process employs transformant strains of *E. coli* containing an expression vector coding for swine growth hormone under the control of a bacteriophage lambda promoter-operator and an expression vector coding for the cI857 temperature-sensitive repressor protein. In the initial growth period, the level of dissolved oxygen in the fermentation medium is maintained at about 20% to 60% saturation and the temperature of the medium is kept between 26° C. and 30° C. Production of swine growth hormone is then induced by raising the temperature of the medium to about 42° C. The temperature is then reduced to about 40° C. to optimize cell growth for the remainder of the induction period, during which the level of dissolved oxygen in the medium is maintained at about 10% to 40% saturation.

21 Claims, 1 Drawing Sheet

FERMENTATION PROCESS FOR THE HIGH LEVEL PRODUCTION OF SWINE GROWTH

BACKGROUND OF THE INVENTION

This invention relates to high level microbial production of swine growth hormone through recombinant DNA technology. This high level production is achieved through high-density fermentation of *E. coli* cells transformed with a recombinant vector carrying a gene encoding swine growth hormone.

Swine growth hormone (SGH) is a protein of 190 amino acids, which is initially synthesized in the anterior pituitary gland as a precursor "pre-growth hormone" having 26 additional amino acids attached at the N-terminus. This 26-amino acid "signal sequence" is processed off during secretion from the pituitary cells, yielding the mature hormone. It has been demonstrated that administration of SGH, purified from pituitary glands, to pigs results in increased growth rates, improved feed-to-animal weight conversion, improved meat quality in terms of nutritional content, and improved carcass quality in terms of increased length and reduced backfat. (See, for example, European Patent Application Publication No. 0 104 920.) The potential economic value of this hormone sparked interest in obtaining SGH in commercial quantities at reasonable cost.

Thus, much work in recent years has focused on obtaining microbial synthesis of this commercially valuable hormone using recombinant DNA technology. Gene cloning and manipulation techniques well known in the art have been used to produce recombinant expression vectors containing SGH-encoding cDNA fused to regulatory regions capable of directing synthesis of SGH in the desired host cells. Microorganisms transformed with these expression vectors have been shown to produce the desired hormone. For example, the cloning of SGH-specific cDNa and construction of expression vectors therefrom is described in European Patent Application Publication No. 0 104 920 (hereinafter referred to as EPO No. 0 104 920). The highest yield of SGH reported in this publication, 32 mg/liter, was achieved in small scale cultures of *E. coli* cells transformed with both an expression vector encoding Δ-7 SGH (an SGH polypeptide lacking the first seven amino-terminal amino acids of the mature hormone) and a plasmid carrying a gene encoding a temperature-sensitive repressor to control SGH synthesis. Large-scale fermentation of any of the transformed strains is not reported. Seeburg et al., (*DNA*, 2:37–45 [1983]) describe the cloning of bovine and porcine (swine) growth hormone cDNA and construction of expression vectors encoding the complete mature hormones (i.e., the "pre" or signal sequence region is removed in vitro during vector construction). *E. coli* cells were transformed with the SGH expression vector, and SGH synthesis was regulated by the plasmid-borne *E. coli* trp regulatory region. It is reported that high density fermentation of the transformed *E. coli* cells yielded approximately 1.5 grams/liter SGH, but no description of the fermentation conditions is given.

Obtaining maximal expression levels of the protein products of cloned genes often involves some trial and error. The genes may be fused to several different regulatory regions and/or transformed into several host cell strains for comparative analyses to find the transformed strain giving the highest production levels of the desired protein. To date, efforts at yield improvement of microbially produced growth hormones have been carried out primarily at the level of genetic manipulations designed to increase cellular expression. There is still a need for the development of commercial scale fermentation processes capable of producing growth hormones in the highest possible yields.

SUMMARY OF THE INVENTION

The present invention provides a method of producing SGH at high levels by fermentation of *E. coli* cells transformed with a recombinant vector containing an SGH-encoding gene. SGH expression is regulated by a temperature-sensitive repressor encoded by a second plasmid which has also transformed the *E. coli* host strain. Using the method of the present invention, we have obtained high density fermentations yielding SGH at 7.2 to 10.7 grams per liter.

This method of producing SGH comprises inoculating an aqueous fermentation medium with a transformant *E. coli* strain containing an expression vector which directs the expression of swine growth hormone under the control of a phage lambda promoter-operator and an expression vector which directs the expression of the λcI857 temperature-sensitive repressor protein. The transformant strain is grown in the fermentation medium for an initial growth period during which the level of dissolved oxygen in the medium is maintained at from about 20% to 60% of saturation and the temperature of the medium is maintained at between about 26° C. and 30° C. This initial growth period is followed by an induction period during which SGH synthesis is induced by raising the fermentation medium temperature to at least about 42° C. to inactivate the temperature-sensitive cI857 repressor protein, then reducing the temperature to about 38° C. to 41° C., preferably about 40° C., and continuing to grow the transformant strain, for the remainder of the induction period with the dissolved oxygen level in the medium maintained at from about 10% to 40% of saturation. The swine growth hormone thus produced is then recovered from the transformant cells.

DETAILED DESCRIPTION OF THE INVENTION

Figure 1:
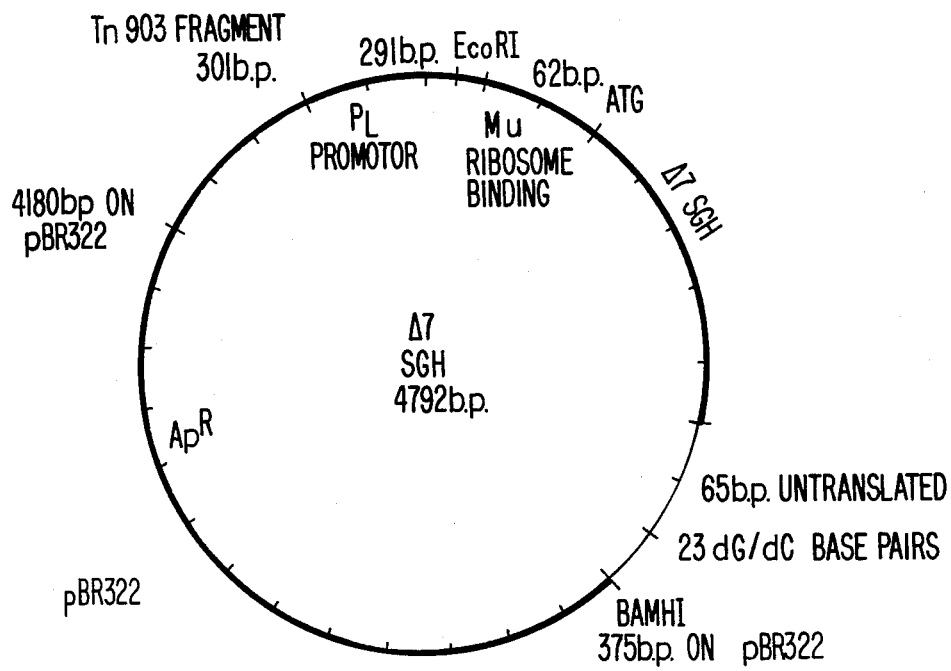
FIG. 1 is a representation of the salient features of plasmid $P_L$-mu-Δ7 SGH, a SGH expression vector which can be used in the method of the invention.

We have developed a method of enhancing SGH production in an *E. coli* strain transformed with an SGH-encoding plasmid. The plasmid which directs SGH expression in the method of the invention can be any suitable SGH-encoding plasmid in which SGH expression is directed by a regulatory region comprising a promoter-operator region derived from bacteriophage λ, preferably the λ$P_L$ promoter-operator region. The regulatory region also contains a Shine-Dalgarno (ribosomal binding) region, which is preferably derived from bacteriophage mu. The SGH-encoding sequence, which is operably fused to the regulatory region, comprises a DNA sequence encoding a polypeptide having the amino acid sequence of SGH or a biologically active fragment or analog thereof. As used herein, the terms "swine growth hormone" and "SGH" include fragments of the hormone which may, for example, have varying portions of the amino terminal end of the hormone deleted, or may have various substitutions or modifications in the SGH sequence which do not destroy the biological activity of the polypeptide. SGH polypeptides lacking various portions of the amino terminal end of the hormone have been shown to retain biological activity (see, for example, European Patent Application Publication No. 0 104 920). In a preferred embodiment of the invention, the SGH-encoding plasmid encodes Δ7 SGH, i.e., a polypeptide corresponding in amino acid sequence to SGH less the first seven amino-terminal amino acids of the mature hormone.

Advantageously, the plasmid also carries a gene encoding a selectable marker, e.g., an antibiotic resistance gene, for selection of cells transformed by the plasmid.

The transformant strain employed in the method of the invention also contains a λcI857 repressor gene. The repressor protein encoded by this temperature-sensitive mutant gene is known to interact with the operators of phage λ gene regulatory regions (including the $P_L$ operator) to prevent transcription of genes off the promoter in the regulatory region.

This repressor protein has been used to regulate synthesis of desired proteins encoded by recombinant vectors in various transformant strains. For example, C. Queen (*J. of Molec. and Appl. Genetics*, 2:1 (1983), H. Kupper (European Patent Application Publication No. 0 076 037) and G. Buell (European Patent Application Publication No. 0 103 395) all describe the use of the cI857 repressor to regulate synthesis of a recombinant vector-encoded desired protein. The cI857 gene is either carried on the vector carrying the gene for the desired protein (and the λ promoter-operator region directing its expression) or on a separate plasmid transformed into the host cells. Synthesis of the desired protein is repressed by cultivating the transformant host cells at temperatures below 32° C. until the desired cell density is reached. These investigators then inactivated the cI857 repressor (thus inducing synthesis of the desired protein) by raising the temperature to 42°–43° C. for the remainder of the cultivation period.

The cI857 gene is used in the method of the invention to control SGH synthesis, and may be carried in the host cell chromosome, on the SGH-encoding plasmid, or on a second plasmid. In a preferred embodiment of the invention, a second plasmid which directs expression of the cI857 repressor protein is transformed into the host strain along with the SGH-encoding plasmid. The cI857 repressor interacting with the λ$P_L$ promoter-operator may be inactivated to some degree at temperatures as low as 37° C. The best results were achieved, however, by inactivating the cI857 repressor by raising the temperature to 42° C. for 1 hour, then lowering it to 40° C. for the remainder of the fermentation.

The host cells may be any transformable *E. coli* strain suitable for high density fermentation and in which the expression vectors used to transform the cells will be stably maintained. Many such strains are known in the art, with one suitable strain being *E. coli* HB101 (Leu Lac pro thi hrs hsm supE recA sm$^r$).

A preferred transformant strain for use in the method of the invention is *E. coli* HB101 strain which has been transformed with plasmids $P_L$-mu-Δ7 SGH and pcI857. The transformant strain, identified as *E. coli* IMC No. 2, has been deposited at the American Type Culture Collection, Rockville, Md., with accession no. ATCC 53031. The plasmid $P_L$-mu-Δ7 SGH is analogous to the plasmid pSGH-Δ7 described in European Patent Application Publication No. 0 104 920, hereinafter referred to as EPO No. 0 104 920, the disclosure of which is incorporated herein by reference.

Plasmid $P_L$-mu-Δ7 SGH, shown in FIG. 1, encodes an SGH polypeptide lacking the first seven amino-terminal amino acids of the mature hormone. Expression of the SGH-encoding sequence is controlled by a regulatory region comprising the phage λ $P_L$ promoter-operator and a Shine-Dalgarno region derived from bacteriophage mu, with an initiation codon (ATG) adjacent (and 5') to the SGH sequence. The plasmid also carries a gene for ampicillin resistance.

Figure 2:
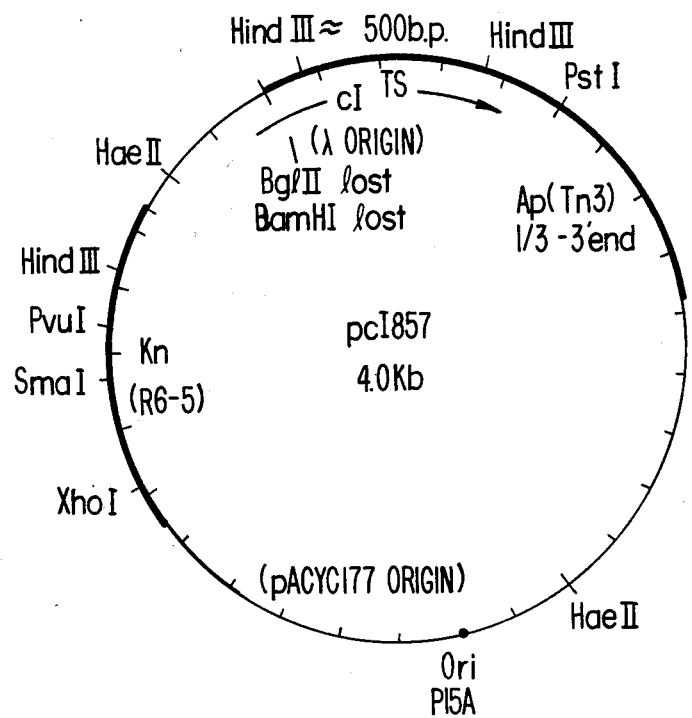
FIG. 2 is a representation of the salient features of plasmid pcI857, which encodes a temperature-sensitive repressor used to control SGH production in the method of the invention.

Plasmid pcI857, shown in FIG. 2, is a multicopy plasmid which encodes the cI857 temperature-sensitive repressor and also carries a kanamycin resistance gene. *E. coli* HB101 cells transformed with both plasmids were selected by growth in Luria broth supplemented with both ampicillin and kanamycin by a procedure similar to that described in EPO No. 0 104 920.

The transformant strain is used to inoculate an aqueous medium contained in a fermentor. The aqueous fermentation medium can be any medium suitable for supporting high density growth of *E. coli*. The medium contains a carbon source, a nitrogen source, salts, and any other nutrients required for cell growth. Suitable carbon sources include, for example, glycerol and hydrated glucose (available commercially as Cerelose ®). Suitable nitrogen sources include, for example, acid hydrolysates of casein (available commercially as Hy-Case Amino and Casamino Acids); enzymatic hydrolysates of casein (commercially available as NZ Amine A, Casatone, Marcor Casein peptone M, and Tryptone), vegetable derived hydrolyzed proteins (such as soybean peptones, hydrolyzed corn gluten and cottonseed peptone); meat peptones; and yeast extracts. Other suitable carbon and nitrogen sources known to those skilled in the art may also be employed. Any components required for retention of plasmids by host cells are added to the medium. For example, the antibiotics ampicillin and kanamycin are added when the transformant strain *E. coli* IMC No. 2 is grown in a fermentor.

Any conventional fermentation equipment known in the art can be used, provided there are means of controlling the medium temperature, of agitating and aerating the medium, and of adding oxygen to the intake air.

The fermentor is inoculated with a culture of the transformant strain. Advantageously, the culture will have been previously incubated at 30° C. for between 8 and 24 hours, preferably between 16 to 20 hours, (or until the $A_{550}$, i.e., the absorbance at 550 nanometers of the culture, is between 2 and 42, preferably above 30) with agitation, for example, at 300 rpm. The culture can be grown in any suitable medium, for example, the ESM-1 and ESM-2 media described below or Luria broth, with ESM-2 media being preferred. The volume of culture used to inoculate the fermentor is between 1/500th and 1/25th, preferably about 1/50th of the volume of medium contained in the fermentor.

In the method of the invention, the fermentation is conducted in two phases. Following inoculation of the fermentation medium with the transformant strain, an initial growth period is conducted during which the level of dissolved oxygen in the medium is maintained at from about 20% to 60% saturation. The dissolved oxygen level decreases as cell density begins to increase rapidly, but is preferably kept above 20% saturation. This may be accomplished by feeding ambient air into the fermentor at a rate sufficient to maintain the dissolved oxygen concentration at the desired level, while also agitating the fermentation medium by any suitable mechanical means. Feeding ambient air at a rate of 0.8 to 1.2, preferably about 1.0, volume of air (STP) per volume of liquid per minute with agitation at 800 to 1200 rpm, preferably about 1000 rpm, is suitable. The agitator is driven by a motor which preferably provides a power input of about 0.5 to 1.5 horsepower per 100 gallons of fermentation medium. The temperature of the medium during the initial growth period is any temperature at which $E.$ $coli$ growth is supported while the cI857 repressor protein is active and SGH expression in the transformant strain is therefore repressed. For the particular transformant strain $E.$ $coli$ IMC No. 2, the temperature is held between 26° C. and 30° C., preferably at about 28° C. to 30° C.

Alternatively, the temperature may first be held at about 28° C. to 30° C. for a portion of the initial growth period, for example, the first 13 hours, and may then be raised gradually to about 35° C. during the remainder of the initial growth period.

The initial growth period is continued until cell density (as measured by the $A_{550}$ of a sample of culture from the fermentor) reaches 20 to 40, which commonly occurs at about 16 to 24 hours after inoculation of the fermentation medium. Good results may also be obtained by continuing the initial growth period until cell densities reach an $A_{550}$ of about 60. During this "extended growth period", the temperature may be gradually raised to 35° C., as described above, or nutrients may be added, as described below. Addition of nutrients may increase the rate of cell growth so that an $A_{550}$ of about 60 can be reached in about 16 hours.

At this point, the second fermentation phase, an induction period, is begun. The temperature of the fermentation medium is raised to at least about 42° C. (preferably 42° C.) and held there for about one hour, thereby inactivating the cI857 repressor protein and inducing production of SGH in the transformant strain. The temperature is then reduced to about 38° C. to 41° C., preferably about 40° C. At this temperature, the cI857 repressor protein is inactive but conditions are more favorable for $E.$ $coli$ growth than at 42° C.

The dissolved oxygen level in the medium is maintained at from about 10% to 40%, preferably above 20%, of saturation during the induction period. Any suitable means of aeration and agitation can be used to maintain this dissolved oxygen level. In a preferred embodiment of the invention, ambient air was fed at a rate of 0.8 to 1.2, preferably about 1.0, volumes of air (STP) per volume of liquid per minute, and the medium was agitated at 800 to 1200 rpm, preferably about 1200 rpm. The agitator is driven by a motor which preferably provides a power input of about 0.5 to 1.5 horsepower per 100 gallons of fermentation medium. Since the rate of oxygen consumption is increased during the induction period, it is preferred to supplement the oxygen present in the ambient air source by feeding oxygen into the fermentor in order to maintain the desired dissolved oxygen level. Any conventional means of providing oxygen to the fermentation medium may be employed. For example, a sparger which is connected to an oxygen source may be inserted directly into the medium or oxygen may be added to the ambient air being fed into the fermentor.

The induction period is continued until cell density reaches an $A_{550}$ of about 80 to 155, preferably 118 to 153. These cell densities are commonly reached at about about 8 to 12 hours after the start of the induction period (i.e., after raising the temperature to 42° C.). Fermentation parameters indicating that SGH synthesis and cell growth are complete include: (1) a significant decrease in oxygen demand, (2) no further increase in cell density ($A_{550}$ values), and (3) NaOH utilization (for pH control) stops.

Nutrients which are depleted from the fermentation medium during cell growth are replenished by any of the methods known in the art. Nutrients may be fed continually or in portions during the fermentation. Preferably, nutrients are added in portions, as needed.

A portion of nutrients may be added at the time of induction of SGH synthesis (i.e., when the temperature is raised to 42° C.), and at least once, preferably twice, during the induction period. For example, a first portion of nutrients may be added at the time of induction (when the $A_{550}$ is between about 20 and 40), and a second portion of nutrients may be added about 5 hours post-induction (when the $A_{550}$ is between about 80 and 90). Alternatively, a first portion of nutrients may be added at the time of induction (when the $A_{550}$ is between about 20 and 40), a second portion of nutrients may be added about 4 hours post-induction (when the $A_{550}$ is between about 70 and 80) and a third portion of nutrients may be added about 6 hours post-induction (when the $A_{550}$ is between about 90 and 100).

Excellent results also may be obtained by adding a first portion of nutrients during the initial growth period, for example, at an $A_{550}$ of about 30 (or about 13 hours post-inoculation) and continuing the initial growth period until the $A_{550}$ reaches about 60. A second portion of nutrients is given at the time of induction (when the $A_{550}$ is about 60, which may be achieved by about 16 hours post- inoculation). Nutrients may then be added in portions once, or preferably twice, during the induction period, as described above.

The nutrients to be added will depend on the composition of the fermentation medium chosen. In general, the nutrients to be added may comprise the carbon source(s) and the nitrogen source(s) present in the fermentation medium into which the transformant strain was inoculated. In one embodiment of the invention, NZ Amine A and glycerol are the nutrients added in portions. In another embodiment of the invention wherein the fermentation medium contains corn gluten hydrolysate, the nutrients added in portions comprise NZ Amine A, glycerol, and corn gluten hydrolysate, as described below.

The SGH produced by the transformant strain may be recovered by any suitable means known in the art. Cells may be harvested from the fermentation medium by, for example, centrifugation. Cells are then lysed by enzymatic, chemical or mechanical means, for example, using sonication, a French press, a homogenizer or treatment with such agents as lysozyme and detergents such as Triton-X-100. SGH may be purified from the cell lysate by any suitable protein purification method, including affinity chromatography, selective precipitation from a solution of a salt such as ammonium sulfate, ion exchange chromatography, isoelectric focusing, or any combination of methods.

The fermentation process of the invention yielded 7.2 to 10.7 grams per liter of Δ7 SGH in the high density fermentations that were achieved. Investigators who previously have worked with *E. coli* strains transformed with $P_L$-mu-Δ7 SGH and pcI857 reported yields of 32 mg/liter Δ7 SGH or less from small cultures, as measured by radioimmunoassay (see EPO No. 0 104 920 where $P_L$-mu-Δ7 SGH is called pSGH-Δ7). Using the method of the present invention, we have successfully enhanced the SGH production levels achieved using this transformant strain.

The method of the invention is described more fully in the examples which follow. The examples are provided to further illustrate the method of the invention and are not to be construed as limiting the scope of the invention.

EXAMPLE I

Conditions for Enhanced Microbial Production of Swine Growth Hormone

Samples of *E. coli* IMC No. 2 cells, to which 10% (v/v) glycerol had been added, were stored under liquid nitrogen or at −85° C. until needed.

A. Inoculation

The inoculum for a 9-liter fermentor charge was obtained by adding the cells to 200 ml of either ESM-1 or ESM-2 medium contained in a 500 ml flask. The pH of the medium was adjusted to a value of 6.8–7.0 and the medium contained about 25 μg/ml each of ampicillin and kanamycin. The flask was closed with two milk filters so that some aeration of the medium could take place while the flask was shaken at 300 rpm for 16–20 hours at 30° C. in a New Brunswick Rotary Shaker.

| Ingredient | ESM-1 | ESM-2 |
| --- | --- | --- |
| NZ Amine A | 16 g/L | 23 g/L |
| Glycerol | 30 | 30 |
| $KH_2PO_4$ | 5 | |
| $(NH_4)_2HPO_4$ | 2.5 | |
| $MgSO_4.7H_2O$ | 7 | 7 |
| $K_2HPO_4$ | | 6 |
| $(NH_4)_2SO_4$ | | 5 |
| $NaH_2PO_4$ | | 3 |
| Na Citrate | | 1 |
| Trace Element Solution* | 20 ml | 20 ml |

*Trace element solution g/L: EDTA 5, $FeCl_3.6H_2O$ 0.5, ZnO 0.05, $CuCl_2.2H_2O$ 0.01, $Co(NO_3)_2.6H_2O$ 0.01, $(NH_4)_2MoO_4$ 0.01.

B. Fermentor

The fermentor was a New Brunswick Microgen with a total volume of 16 liters. Nine liters of liquid medium was initially charged to the fermentor plus 180 ml of inoculum.

C. Fermentation Medium

The composition of the initial 9 liters of medium is shown below:

| Product | Concentration (Grams per 9 Liters) |
| --- | --- |
| NZ Amine A-Sheffield | 250 |
| Glycerol | 500 |
| $(NH_4)_2SO_4$ | 50 |
| $K_2HPO_4$ | 60 |
| $NaH_2PO_4$ | 30 |
| Na Citrate | 10 |
| $MgSO_4.7H_2O$ | 70 |
| Hodag K-67 antifoam | 4 ml |
| $FeCl_3.6H_2O$ | 0.1 |
| ZnO | 0.01 |
| $CuCl_2.2H_2O$ | 0.002 |
| $Co(NO_3)_2.6H_2O$ | 0.002 |
| $(NH_4)_2MoO_4$ | 0.002 |
| EDTA (disodium salt) | 1.0 |

The medium was sterilized for 20 minutes at 121° C. and the pH was adjusted to 6.8 with NaOH. The pH was maintained by additions of NaOH, as necessary, during fermentation.

To the medium 250 mg each of ampicillin and kanamycin were added. The solution of antibiotics was sterilized by filtration.

Dissolved oxygen (DO) concentration was constantly monitored throughout the fermentation with a galvanic probe connected to a strip recorder. During induction, DO was maintained at 10–40% saturation (1–4 ppm) by enriching the inlet air with oxygen gas. A gas tank equipped with an oxygen regulator was used to control the flow of oxygen into the inlet air. After the gases were mixed, the oxygen-enriched air was filtered and entered the fermentor vessel through a sparger.

D. Nutrient Feedings

At the time of induction ($A_{550}=37$), i.e., when the temperature was raised to 42° C., nutrients were added to the fermentation medium. 250 g NZ Amine A and 200 g glycerol in approximately one liter water, were added. An additional feeding of 100 g NZ Amine A and 100 g of glycerol was given 5 hours post-induction ($A_{550}=84$).

E. Fermentor Operation

The operating conditions that gave us our best results are set forth in this section.

1. Growth Period 16–24 Hours a. Temperature of medium=28°–30° C.
b. Agitator speed: 1000 RPM.
c. Energy input by the agitator: 0.5–1.5 horsepower per 100 gallons.
d. Aeration rate: 10 L (STP) per minute.
e. Back pressure: 5 lbs per in².
f. Dissolved oxygen: Above 20% of saturation value.
g. Absorbance of light at wavelength 550 nm ($A_{550}$) by a sample of the fermenting medium: 20–40 at end of initial growth period.

2. Induction Period a. Temperature of medium.
  (1) 42° C. for the first hour of induction.
  (2) 40° C. for remainder of induction period.
b. Agitator speed: 1200 RPM.
c. Energy input by agitator: 0.5–1.5 horsepower per 100 gallons.
d. Aeration rate: 10 L (STP) per minute.
e. Back pressure: 3–6 lbs per in².
f. Dissolved oxygen: preferably above 20% of saturation. In order to obtain these values, the inlet air is enriched with oxygen.
g. Final absorbance: $A_{550}$ of 118–153.

F. Results

For HPLC analysis, fermentor broth samples were collected by centrifugation (10–15,000×g, 15 min.) and bacteria were resuspended in 4–5 volumes of buffered guanidine (8M guanidine HCl, 100 mM glycine NaOH buffer, pH 9.8, 5 mM reduced glutathione). The suspension was allowed to sit for 20–30 min. and was then homogenized for 15–20 seconds with a model SDT-1810 Tek-Mar tissue mizer. Insoluble debris was removed by centrifugation as above and the clarified SGH extract was assayed by HPLC. Some extracts were diluted 1:2 with guanidine buffer before HPLC assay.

| | Final Assay of Fermentation Medium for $\Delta7$ SGH. Assay Method: High Performance Liquid Chromatography | | | |
|---|---|---|---|---|
| Run No. | Back Pressure Lbs. per in$^2$ | Final Absorbance $A_{550}$ nm | Number of Cells per ml (Final) | Swine Growth Hormone Grams per Liter (HPLC) |
| 94 | 5 | 118 | $5 \times 10^{10}$ | 7.23 |

EXAMPLE II

Alternative Fermentation Conditions for Enhanced Microbial Production of Swine Growth Hormone The procedures of Example I were followed, with the exception of steps C and D. Alternative procedures for steps C and D, and the results, are given below:

C. Fermentation Medium

| Product | Concentration (Grams/9 Liters) | |
|---|---|---|
| Corn Gluten Hydrolysate | 975 ml | (equal to 250 g corn gluten meal before hydrolysis) |
| NZ Amine A | 125 g | |
| Glycerol | 500 g | |
| (NH$_4$)$_2$SO$_4$ | 50 | |
| K$_2$HPO$_4$ | 60 | |
| NaH$_2$PO$_4$ | 30 | |
| Na Citrate | 10 | |
| MgSO$_4$.7H$_2$O | 70 | |
| Hodag K-67 antifoam | 4 ml | |
| FeCl$_3$ | 0.1 g | |
| ZnO | 0.01 g | |
| CuCl$_2$.2H$_2$O | 0.002 g | |
| Co(NO$_3$)$_2$.6H$_2$O | 0.002 g | |
| (NH$_4$)$_2$MoO$_4$ | 0.002 g | |
| EDTA | 1 g | |
| Ampicillin | 0.250 g | } sterile filtered |
| Kanamycin | 0.250 g | |

*Corn gluten hydrolysate prepared by stirring 1500 g corn gluten meal (Grain Processing Corporation - 61% proT) and 75 ml Alcalase ® 2.5 (Novo Laboratories) in 5 liters of distilled water. Temperature was controlled at 50° C. and pH controlled at 8.5 with NaOH. Hydrolysis time was overnight (16 hours). Reaction mixture was centrifuged; final volume = 5850 ml.

Nutrient Feedings

A induction ($A_{550}$=30), 125 g NZ Amine A, 975 ml of corn gluten hydrolysate and 200 g of glycerol were added. Additonal feedings of 50 g of NZ amine A, 390 ml corn gluten hydrolysate and 100 g glycerol were added at 4 hours ($A_{550}$=74) and 6 ($A_{550}$=95) hours post induction.

E. Results

| | Final Assay of Fermentation Medium for $\Delta7$ SGH. Assay Method: High Performance Liquid Chromatography | | | |
|---|---|---|---|---|
| Run No. | Back Pressure Lbs. per in$^2$ | Final Absorbance $A_{550}$ nm | Number of Cells per ml (Final) Estimated | Porcine Growth Hormone Grams per Liter (HPLC) |
| 102 | 5 | 153 | $5 \times 10^{11}$ | 10.7 |

What is claimed is:

1. A method of producing swine growth hormone which comprises: inoculating an aqueous fermentation medium with a culture of a transformant E. coli strain containing an expression vector which directs the expression of swine growth hormone under the control of a phage lambda promoter-operator and an expression vector which directors the expression of the cI857 temperature-sensitive repressor protein; growing the transformant strain in the fermentation medium for an initial growth period during which the level of dissolved oxygen in the medium is maintained at from 20% to 60% of saturation and the temperature of the medium is maintained at 26° to 30° C.; raising the temperature of the fermentation medium to at least about 42° C. to inactivate the temperature-sensitive repressor protein, thereby initiating an induction period during which swine growth hormone is produced; then, after inactivation of the repressor protein, lowering the temperature of the medium to below the temperature necessary to completely inactivate the repressor protein by reducing the temperature to about 38° C. to 41° C. and then continuing to cultivate the transformant strain at a temperature below the temperature necessary to completely inactivate the repressor protein for the remainder of the induction period during which the level of dissolved oxygen in the medium is maintained at from 10% to 40% of saturation; and recovering the swine growth hormone from the transformant cells.

2. A method as claimed in claim 1, wherein the initial growth period is effected for a period of from about 16 hours to about 24 hours.

3. A method as claimed in claim 1, wherein the temperature during said initial growth period is maintained at about 28° C. to 30° C.

4. A method as claimed in claim 1, wherein the temperature is increased to at least about 42° C. to inactivate the temperature-sensitive repressor protein when the cell density in the fermentation medium has reached an $A_{550}$ of from 20 to 40.

5. A method as claimed in claim 1, wherein the temperature is increased to at least about 42° C. to inactivate the temperature-sensitive repressor protein when the cell density in the fermentation medium has reached an $A_{550}$ of about 60.

6. A method as claimed in claim 1, wherein following inactivation of the repressor protein, the temperature is reduced to about 40° C. for the remainder of the induction period.

7. A method as claimed in claim 1, wherein the transformant strain is one which produces a biologically active fragment of swine growth hormone in which the first seven amino-terminal amino acids of the mature protein are deleted.

8. A method as claimed in claim 1, wherein the induction period is effected for a period of about 8 to 12 hours.

9. A method as claimed in claim 1, wherein the induction period is effected until cell density in the fermentation medium has reached an $A_{550}$ of from about 80 to 155.

10. A method as claimed in claim 1, wherein the transformant strain is *E. coli* IMC No. 2, ATCC 53031.

11. A method as claimed in claim 1, wherein nutrients are fed to the fermentation medium in portions.

12. A method as claimed in claim 11, wherein a first portion of nutrients is added to the fermentation medium when the cell density in the fermentor reaches an $A_{550}$ of from 20 to 40, a second portion of nutrients is added when the cell density reaches an $A_{550}$ of from 70 to 80 and a third portion of nutrients is added when the cell density reaches an $A_{550}$ of from 90 to 100.

13. A method as claimed in claim 11, wherein a first portion of nutrients is added to the fermentation medium at the beginning of the induction period, about 4 hours after the beginning of the induction period and about 6 hours after the beginning of the induction period.

14. A method as claimed in claim 11, wherein a first portion of nutrients is added to the fermentation medium when the cell density reaches an $A_{550}$ of about 20 to 40 and a second portion is added when the $A_{550}$ reaches about 80 to 90.

15. A method as claimed in claim 11, wherein nutrients are added to the fermentation medium in portions at the beginning of the induction period and about five hours after starting the induction period.

16. A method as claimed in claim 1, wherein the level of dissolved oxygen during said induction period is maintained above about 20% of saturation by addition of oxygen to the fermentor.

17. A method as claimed in claim 1, wherein the dissolved oxygen level is maintained during the initial growth period by feeding ambient air to the fermentor at a rate of about 0.8 to 1.2 volumes of air per volume of liquid per minute and mechanically agitating the fermentation medium with an agitator having a power input of about 0.5 to 1.5 horsepower per 100 gallons of fermentation medium.

18. A method as claimed in claim 17, wherein ambient air is fed to the fermentor at a rate of about 1.0 volumes of air per volume of liquid per minute.

19. A method as claimed in claim 17, wherein the dissolved oxygen level is maintained during the induction period by feeding ambient air to the fermentor at a rate of about 0.8 to 1.2 volumes of air per volume of liquid per minute and mechanically agitating the fermentation medium with an agitator having a power input of about 0.5 to 1.5 horsepower per 100 gallons of fermentation medium, while simultaneously feeding oxygen to the fermentation medium.

20. A method as claimed in claim 19, wherein ambient air is fed to the fermentor at a rate of about 1.0 volumes of air per volume of liquid per minute.

21. A method of producing swine growth hormone which comprises: inoculating an aqueous fermentation medium with a culture of a transformant *E. coli* strain containing an expression vector which directs the expression of swine growth hormone under the control of a phage lambda promoter-operator and an expression vector which directs the expression of the cI857 temperature-sensitive repressor protein; growing the transformant strain in the fermentation medium for an initial growth period during which the level of dissolved oxygen in the medium is maintained at from 20% to 60% of saturation and the temperature of the medium is maintained at 26° to 30° C.; raising the temperature of the fermentation medium to at least 42° C. to inactivate the temperature-sensitive repressor protein, thereby initiating an induction period during which swine growth hormone is produced; reducing the temperature to 38° C. to 41° C. and continuing to cultivate the transformant strain for the remainder of the induction period during which the level of dissolved oxygen in the medium is maintained at from 10% to 40% of saturation; and recovering the swine growth hormone form the transformant cells.

* * * * *

UNITED STATES PATENT AND TRADEMARK OFFICE
CERTIFICATE OF CORRECTION

PATENT NO.  :  4,788,144
DATED       :  NOVEMBER 29, 1988
INVENTOR(S) :  JAMES R. McMULLEN

It is certified that error appears in the above-identified patent and that said Letters Patent is hereby corrected as shown below:

Front page, [54] in the title, insert --HORMONE -- after "GROWTH"

Front page, Column 2, Primary Examiner, delete "Taneholtz" and substitute therefor -- Tanenholtz --, Column 1, line 2, after "GROWTH" insert -- HORMONE--;

line 39, delete "cDNa" and substitute therefor -- cDNA --;

Column 9, line 62, delete delete "A" and substitute therefor -- At --;

line 64, delete "Additonal" and substitute therefor -- Additional --

Signed and Sealed this

Twentieth Day of March, 1990

Attest:

JEFFREY M. SAMUELS

Attesting Officer      Acting Commissioner of Patents and Trademarks